United States Patent [19]

Sorsa et al.

[11] Patent Number: 5,736,341
[45] Date of Patent: Apr. 7, 1998

[54] METHODS AND TEST KITS FOR SPECIFIC AND SENSITIVE DIAGNOSING OF PERIODONTAL DISEASES

[75] Inventors: Timo Arto Sorsa; Sari Hannele Tikanoja, both of Helsinki; Leila Christina Lundqvist, Espoo, all of Finland

[73] Assignee: Oy Medix Biochemica AB, Kauniainen, Finland

[21] Appl. No.: 487,656

[22] Filed: Jun. 7, 1995

[30] Foreign Application Priority Data

Aug. 26, 1994 [FI] Finland ................... 943939

[51] Int. Cl.$^6$ ................ G01N 33/53; G01N 33/537; G01N 33/543; G01N 33/554; G01N 33/551; G01N 33/546; C07K 16/00; C12P 21/08

[52] U.S. Cl. ................ 435/7.1; 435/7.32; 435/7.4; 435/7.9; 435/7.92; 435/810; 435/325; 435/326; 435/338; 435/975; 435/974; 436/501; 436/518; 436/524; 436/523; 436/533; 436/528; 436/534; 436/819; 436/808; 436/909; 530/387.1; 530/388.1; 530/388.26; 530/391.1; 530/389.1; 422/101

[58] Field of Search ............ 422/101; 530/387.1, 530/388.1, 388.26, 391.1, 389.1; 435/7.1, 7.32, 7.4, 7.9, 7.92, 810, 975, 974, 325, 326, 338; 436/501, 518, 524, 523, 533, 528, 534, 819, 808, 909

[56] References Cited

PUBLICATIONS

Chemical Abstracts 114:181010u.
Chemical Abstracts 119:154562x.
Chemical Abstracts 116:39607s.
Chemical Abstracts 101:34981q.
Chemical Abstracts 97:177480k.
Chemical Abstracts 113:147895f.
Chemical Abstracts 113:226795b
McCullough, J. Clin. Periodontal, 21:497–506 (1994).
Yoshida, Kokubyo Gakkai Zasshi, vol. 60 p. 121, 1993.
Page, J. Periodontol. vol. 63 p. 356, 1992.
Clark et al, Matrix vol. 12 p. 475, Dec. 1992.
Bergmann et al, J. Clin. Chem. Clin. Biochem. vol. 27 p. 351, 1989.
Hasty et al, J. Exp. Med. vol. 159 p. 1455, May 5, 1984.

*Primary Examiner*—Sheela Huff
*Attorney, Agent, or Firm*—Birch, Stewart Kolasch & Birch, LLP

[57] ABSTRACT

Methods and test kits are described which provide a reliable, sensitive and selective assessment of periodontal disease activity, peri-implantitis or HIV(+)-infection/AIDS-disease related periodontal diseases. The preferred methods and test kits are constructed to be easy and rapid chair-side tests. The method is based on the preparation and use of monoclonal antibodies which recognize the active mammalian matrix metalloproteinase-8 (MMP-8) and is capable of differentiating between said active matrix metalloproteinase-8 and its inactive proform.

24 Claims, No Drawings

METHODS AND TEST KITS FOR SPECIFIC AND SENSITIVE DIAGNOSING OF PERIODONTAL DISEASES

BACKGROUND OF THE INVENTION

THE TECHNICAL FIELD OF THE INVENTION

The present invention relates to methods and test kits for diagnosis of periodontal disease activity in mammals, especially in human beings. The methods of the invention provide for rapid chair-side diagnosis of periodontitis, peri-implantitis and HIV(+)-infection/AIDS-disease related periodontal diseases.

THE BACKGROUND OF THE INVENTION

Periodontal diseases are a major problem in the human dentition. In fact, more teeth are lost from periodontal disease than from dental caries. Thus, there is a great need for reliable diagnostic tests for periodontal disease.

Periodontal disease comprises a group of inflammatory disorders originating from infections affecting the gingiva (gum) and the alveolar (jaw) bone structures supporting the teeth. The primary cause of periodontal diseases is bacterial plaque attached to the teeth. This causes inflammation of the gum which may result in destruction of the actual tooth-supporting structure and bone. In periodontal disease, there is usually a large accumulation of bacteria in plaque, both above (supragingival) and below (subgingival) the gum line. The plaque can calcify and form calculus deposits. The calculus deposit and associated plaque can create a "pocket" between the teeth and the gingiva which is characteristic of the periodontal disease.

Gingivitis (gum inflammation) is distinguished from periodontitis in that in gingivitis, gingiva are inflamed but no deep (>4 mm) periodontal pockets are detectable; thus, no irreversible destruction of tooth supporting structures is associated with gingivitis. Periodontitis is characterized by inflamed gingiva and destruction of tooth supporting structures; however, periodontitis can be missed in clinically-healthy-looking gingiva.

Several methods for detecting periodontal disease have been developed (Armitage, G. C., C.D.A. Journal 36, 35–41, 1993). However, none of the presently available detection methods is sufficiently accurate and specific to provide a reliable tool for diagnosing periodontal disease activity, assessing peri-implantitis and HIV(+)-infections/AIDS-related periodontal diseases.

Especially, several attempts to develop methods for assessing progressing periodontitis as discussed below have been tested but none of them have been found to be satisfactory enough to create a rapid and reliable chair-side test.

Visual examination

When gingiva (gums) are affected by periodontal disease, color change (from pink to red), texture alterations (redness and swelling), and an increased tendency to bleed (in that particular gingival and sulcular/sulcus area) can be detected. Advanced stage periodontal disease is frequently associated with increased tooth mobility and drifting of the teeth.

However, some forms of periodontal disease such as localized juvenile periodontitis (LJP) can have a treacherous nature and a misleading clinical course. Thus, active local periodontitis is not always detectable by visual examinations. Consequently, biochemical adjunctive means to help the clinical diagnosis of juvenile periodontitis would be desirable and helpful for prompt and adequate early diagnosis especially in case of young patients.

Clinical assessment of periodontal status and probing of periodontal lesions

Currently, periodontal disease is diagnosed by clinical observation of indicators such as presence and depths of periodontal pockets, loss of attachment of the teeth to the bone, and papillary bleeding of the gums. Clinical observations, however, are not always reliable indicators. For example, deep periodontitis pockets containing putative periodontal pathogens are not necessarily indicative of disease activity or periodontal tissue destruction.

Periodontal attachment levels can be assessed by means of a graduated periodontal probe and expressed as the distance from the cement enamel junction to the bottom of the gingival pocket. The longer distance for each tooth surface is recorded and may be included in the periodontium chart. Pocket depth values <4 mm are excluded from the chart as falling within normal variations. Thus, pockets >4 mm are considered as periodontitis pockets or periodontitis lesions.

As a measurement technique, periodontal probing has several sources of error. The extent of probe penetration varies with insertion force, inflammatory status of the periodontal tissues, and diameter of probe tip. Measurement errors resulting from thickness of the probe, contour of the tooth surface and improper angulation of the probe can be reduced or avoided by the selection of a proper instrument and careful management of the examination procedure. More difficult to avoid, however, are errors resulting from variations in probing force and inflammation of the periodontal tissues. The measurement errors limit the accuracy and reproducibility.

Noteworthy, gingivitis or gum inflammation is distinguished from periodontitis by the facts that in gingivitis, unlike periodontitis, gingiva is inflamed but no deep (>4 mm) periodontal pockets can be detected; thus, no irreversible degradation (destruction) of tooth supporting structures either detected by probing and/or radiographically is associated with gingivitis. Periodontitis is characterized by inflamed gingiva and destruction of tooth supporting structures; however, periodontitis can well exist under the "clinically-healthy-looking" gingiva.

As a conclusion it is clear that clinical observations are not always reliable indicators. A further problem is the difficulty to assess an active progressing periodontal disease because in some cases deep peridontitis pockets—even harbored by putative periodontopathogens—are not necessarily active in regard to the inflammatory periodontal tissue destruction. Thus, the existing tests are not reliable as regards to inflammatory periodontal tissue destruction and there is no reliable, inexpensive and objective means for determining whether or not the periodontal pocket is active.

The lack of a diagnostic test revealing and monitoring periodontal disease activity has been a serious problem, particularly in view of the severity of the corrective measures typically required to be taken to treat periodontal disease.

Automated periodontal probes have also been developed. The primary advantage is controlled insertion force, reproducibility, and direct data entry. The main disadvantages include reduced tactile sense of operator and patient discomfort.

Radiographic evaluation

Sequential radiographic images have also been used to evaluate periodontal disease activity. The loss of bone density at the alveolar crest is frequently a sign of progression of periodontitis.

The height of the alveolar (jaw) bone and the outline of the bone crest can be examined in the radiographs. The radiographs provide information of the height and configuration of the interproximal alveolar bone. However, the radiographic assessment of the periodontal disease activity has drawbacks. Even with an excellent set of films and an experienced examiner, the unaided eye can only detect changes in bone after 30–50 percent of the bone mineral has been lost. Cover structures (bone, tissue, teeth) often make it difficult to properly identify the outlines of buccal and lingual alveolar crests. The analysis of radiographs is to be combined with a detailed evaluation of the pocket depths and the attachment level data to obtain a correct and exact diagnosis. Upon recalls (examinations of treated periodontitis patients) radiographic examination is required.

In summary, periodontal probes and radiographs measure two separate components in the progression of periodontitis. One provides an estimate of the attachment loss of soft tissue from the tooth surface and the other measures loss of bone density.

In addition to periodontal probing, biological (microbial and biochemical) tests have been designed to provide information associated with progressing periodontal lesions. These biological periodontitis tests fall into four general categories and are designed to detect the presence of 1) substances associated with putative pathogens, 2) host-derived enzymes, 3) tissue breakdown products, and 4) inflammatory mediators.

Tests for presence of putative periodontal pathogens

Much work has been done to determine which microorganism(s) are associated with progressing periodontitis (Armitage, G. C., Periodontal diagnostic aids, C.D.A. Journal 36, 35–41, 1993). In untreated patients with periodontitis the following bacteria (in various combinations) have been suggested as putative pathogens: spirochetes (such as *Treponema denticola*), *Porphyromonas* (Bacteroides) *gingivalis, Bacteroides forsythus, Prevotella* (Bacteroides) *intermedia, Campylobacter rectus* (*Wolinella recta*), *Eikenella corrodens, Actinobacillus actinomycetemcomitans, Fusobacterium nucleatum, Capnocytophaga sputigena, Peptostreptococcus micros, Streptococcus mitis,* Selenomonas sp., Eubacterium sp. and Haemophilus sp. These organisms have been identified in subgingival plaque samples by cultural analysis, microscopic examination, and by DNA probe analysis (Armitage, G. C., C.D.A. Journal 36, 35–41, 1993).

The BANA/BAPNA-test, based on hydrolysis of benzoyl-arginine-naphtylamide/benzoyl-arginine-p-nitroanilide, has identified the same putative pathogens (Armitage, C. G., C.D.A. Journal 36, 35–41, 1993). Since it is not known with certainty which of these organisms (if any) are responsible for the progression of periodontitis, their presence may not reflect actual periodontal disease activity.

Tests based on host-derived enzymes

The tissue destruction associated with the progression of periodontal disease/periodontitis lesions could be due to the independent and cooperative action of various host and bacterial derived proteolytic enzymes. During the development and progression of periodontitis lesions, various enzymes including matrix metalloproteinases (MMPs), elastase, cathepsins and trypsin-like proteinases etc. are released from triggered host cells. To some extent the proteinases may also be derived from oral bacteria (Uitto, V. J., et al., Proc. Finn. Dent. Soc., 83, 119–130, 1987). Therefore, several enzymes of this type have been suggested as biochemical markers for monitoring the progression and activity of periodontal disease (Armitage, C. G., C.D.A. Journal, 36, 35–41, 1993).

Test methods based on identification and measurement of enzyme activities have been developed. For example, aspartate aminotransferase (ASAT) has been associated with periodontal disease. This enzyme has been measured in gingival crevicular fluid, an inflammatory exudate of adjacent gingiva known to reflect the actual gingival cell tissue health (Page, R. C., J. Periodont. Res. 26, 230–242, 1991). ASAT is, however, released by almost all damaged cells in various periodontal tissues and is also present in blood in significant amounts. Therefore, a gingival crevicular fluid ASAT test is hampered by high non-specific background.

False positives caused by enzymes released in conditions other than active periodontal disease are a major problem when using most of the other suggested enzymes (e.g. β-glucuronidase, lactate dehydrogenase, arylsulfatase, and some proteinases). Chair-side tests have been developed for gingival fluid elastase (Prognostick, Dentsply Corp., York, Pa.) and general proteinase activities (Periocheck®, Advanced Clinical Technologies Inc., Westword, Mass.). Both these tests lack specificity. The synthetic peptides and gelatin used as substrates are degraded by almost all human and bacterial proteinases. Therefore, high background activities, false positive, and false negative results have been found when enzyme activity is correlated with the clinical course of periodontal disease as compared with periodontally healthy controls.

A chair-side colorimetric protease assay system has been suggested for diagnosing periodontal diseases from saliva/mouthrinse, gingival crevicular fluid and dental plaque samples (Periocheck®, Advanced Clinical Technologies Inc., Westword, Mass.) has been developed.

The test known as the BANA/BAPNA-test, is based on hydrolysis of benzoyl-arginine-naphtylamide/benzoyl-arginine-p-nitroanilide. Hydrolysis results in red-orange color that indicates the presence of anaerobic oral bacteria such as *Porphyromonas gingivalis, Treponema denticola* and *Bacteroides forsythus* (Armitage, C. G., C.D.A. Journal, 36, 35–41, 1993). These organisms are thought to release trypsin-like proteases capable of hydrolysing the synthetic BANA/BAPNA-peptide substrates. However, this test is not specific solely to bacterial proteinases. Many host cell derived proteinases (such as trypsins, trypsin-like proteinases, mast cell tryptases etc.) have similar specificities for BANA/BAPNA-peptides (Ingman, T., et al., Oral Microbiol. Immunol. 8, 298–305, 1993). Human cell-derived trypsin-like proteinases in periodontitis gingival crevicular fluid have been shown (Sorsa, T., et al., J. Dent. Res. 71, 732, 1992). Thus, a problem with this test is that it does not distinguish between host-cell derived and bacterial proteinases.

In summary, in the above-described assays, because of the involvement of various host and bacterial derived proteinases in the degradation of non-specific synthetic or natural substrates, such as gelatin, false negative and positive results often occur.

Measurement of tissue breakdown products

One of the major features of periodontitis is the destruction of the extracellular matrix (i.e. collagen) of the periodontium. Type I and III collagens are the predominant collagen types present in periodontium.

Increased concentrations of hydroxyproline and glycosaminglycans have been shown in gingival crevicular fluid of periodontitis patients. Specific N- and C-terminal collagen telopeptides have been studied in periodontitis gingival crevicular fluid. These collagen type I and III propeptides in gingival crevicular fluid are suggested to reflect both gingival collagen synthesis and degradation (Talonpoika, J., Ann. Univ. Turku, Serie D 142, 1994). However, instead of reflecting the gingival collagen degradation they may reflect more efficient collagen synthesis/turnover in general, and have been valuable when monitoring periodontal healing after periodontal treatment rather than actual periodontal destruction associated with active periodontal disease progression (Talonpoika, J., et al., J. Clin. Periodontol. 21, 320–333, 1994).

Measurement of inflammatory mediators

Periodontal tissues and especially some distinct cells connected with gingivitis and periodontitis are known to produce a variety of inflammatory mediators. Some of these have been suggested as biochemical/immunological markers in the assessment of disease activity (Page, R. C., J. Periodont. Res. 26, 533–546, 1991). Increased amounts of these inflammatory mediators are detected in diseased gingival tissue and gingival crevicular fluid relative to periodontally healthy gingiva and gingival crevicular fluid (Page, R. C., J. Periodont. Res. 26, 533–546, 1991). Tumor necrosis factor-$\alpha$, interleukin-1$\beta$ and prostaglandin E2 have been subject of research (Page, R. C., J. Periodont. Res. 26, 533–546, 1991). As these mediators reflect the activity of the inflammatory process, they show promise as markers. Yet none of them has proven to be specific enough to periodontal disease. Nor have rapid tests been developed. In vitro these inflammatory mediators are known to be capable of inducing de-novo MMP-expression by resident oral cells (gingival fibroblasts and keratinocytes) (Birkedal-Hansen, H., J. Periodontol. 64, 474–484, 1993). In vivo, increased amounts of the inflammatory mediators in periodontitis gingiva and gingival crevicular fluid are not associated with associated with increased amounts of fibroblast-type MMPs. These types of MMPs in contrast to the PMN-type MMPs, are expressed and produced by resident gingival/oral fibroblasts and epithelial cells. Neutrophil-derived MMPs and elastase are found in periodontitis gingiva and gingival crevicular fluid (Suomalainen, K., Thesis, Univ. Helsinki, 1993; Ingman, T., Thesis, Univ. Helsinki, Finland, 1994). Therefore, the relationships of the inflammation mediators (tumor necrosis factor-$\alpha$, interleukin-1-$\beta$ and prostaglandin E2 etc.) to MMP-dependent periodontal tissue destruction despite promising in vitro results (Birkedal-Hansen, H., J. Periodontol. 64, 474–484, 1993) is unclear (Sorsa, T., et al., Ann. N.Y. Acad. Sci. 732, 112–131, 1994).

Matrix metalloproteinases (MMPs) in periodontal diseases

Enzymatic degradation of periodontal connective tissue accounts for various alternations that are characteristic of diseased periodontal tissues. These include the net reduction of collagen(s), decreased strength and increased permeability of periodontal/gingival tissue, and alveolar bone loss.

Loss of collagen can result from changes in collagen metabolism. The rate of synthesis by fibroblasts may be decreased in inflamed tissue; the collagen synthesized may include defects in molecular structure of fiber formation. These changes would render collagen more susceptible to proteolytic degradation. It has been shown that polymeric collagen fibrils containing intermolecular crosslinks are considerably more resistant to proteolytic/collagenolytic degradation than are soluble collagen fibrils.

Collagenolytic enzymes (collagenases, gelatinases and stromelysins, members of the matrix metalloproteinase (MMP) family) are a host cell-derived proteinase group that has been thoroughly studied in the context of periodontal disease. In culture conditions, explants of inflamed gingiva secrete more collagenase than do explants from clinically healthy gingiva. A number of lines of in vivo evidence implicate host-cell derived matrix metalloproteinases (MMPs) in human periodontal tissue destruction (Birkedal-Hansen, H., J. Periodontal. 64, 474–484, 1993). Evidence includes elevated collagenase activity (MMP-1 and MMP-8) and gelatinases (MMP-2 and MMP-9) in extracts of inflamed gingival tissues, gingival crevicular fluid and salivary/mouthrinse-samples of periodontitis patients (Sorsa, T., et al., Ann. N.Y. Acad. Sci., 732: 112–131, 1994). The activities of these proteinases have been found to be positively correlated with the severity of periodontal inflammation and pocket depth at the periodontitis lesion sites donating these proteinases to gingival extracellular matrix and adjacent gingiva (Sorsa, T., et al., Ann. N.Y. Acad. Sci., 732: 112–131, 1994). Further, the relative amount of these proteinases recovered in active rather than latent form appears to increase with the greater severity of the periodontal disease (Suomalainen, K., Thesis, Univ. Helsinki, Finland, 1993). Further, the activities of these MMPs in periodontitis sites decrease after instrumentation therapy (scaling and root planing) (Ingman, T., Thesis, Univ. Helsinki, Finland, 1994). Further, increased collagenase activity has been found in gingival crevicular fluid during experimental gingivitis (Sodek, J., et al., Matrix 12 (Suppl. 1), 352–362, 1992). Finally, more collagenase can be extracted from inflamed human gingiva than from less inflamed gingiva (Sorsa, T., Thesis, Univ. Helsinki, Finland, 1989). These results are thought to reflect changes in mammalian MMP activity because the proteinases recovered from diseased sites degrade triple helical collagen into the ¾- and ¼-fragments that are characteristic of mammalian collagen cleavage (Sorsa, T., Thesis, Univ. Helsinki, Finland, 1989; Sodek, J., et al., Matrix 12 (Suppl. 1), 352–362, 1992). Recent studies on collagenases in gingivitis/periodontitis in gingiva, gingival crevicular fluid, and saliva have utilized the difference in cleavage patterns of collagen by vertebrate and bacterial collagenase to identify the origin of the collagenases (Sorsa, T., et al., Ann. N.Y. Acad. Sci., 732: 112–131, 1994). For example, collagen type I was incubated with gingival extracts of inflamed human gingiva, and the reaction products were analyzed. The results consistently showed a cleavage pattern characterized by human rather than bacterial collagenase. Thus, collagenase of gingival crevicular fluid samples has been proved to originate mainly from human cells and not from bacteria (Sorsa, T., et al., Ann. N.Y. Acad. Sci., 732: 112–131, 1994). Recent studies have also shown that salivary and dental plaque collagenases from human supragingival and subgingival dental plaque samples are of human origin and has functional and immunological characters of MMP-8 in active form (Sorsa, T., et al., J. Clin. Perio., in press, 1995). Thus, it appears that collagenase in periodontal disease is derived mainly from the host.

Further characterization of gingival tissue, gingival crevicular fluid, and salivary collagenases have revealed that the predominant source of the enzymes are polymorphonuclear neutrophilic leucocytes (PMN) present in periodontal inflammation. This is based on studies of the substrate specificity against type I–III collagens, response to procollagenase activators, and Western-blot and immunochemical analysis using specific anti-MMP antibodies (Sorsa, T., et al., Ann. N.Y. Acad. Sci. 732, 112–131, 1994). Tonetti, M. S., et al., have recently noticed that transcripts of neutrophil collagenase (MMP-8) can be found in inflamed human gingival tissue (Tonetti, M. S., et al., J. Periodont: Res. 28, 511–513, 1993.).

If measured as total gingival crevicular fluid (GCF) and salivary collagenase or gelatinase activities, these proteinases have been found to be positively correlated with inflamed gingival tissue collagenase and gelatinase activities and thus reflect the periodontal tissue destruction and periodontal disease activity (Kinane, Curr. Op. Dent. 2, 25–32, 1992). Periodontal treatment results in decreased gingival crevicular fluid, salivary/mouthrinse PMN MMP-activities (Sorsa, T., Thesis, Univ. Helsinki, 1989: Suomalainen, K., Thesis, Univ. Helsinki, Finland, 1993; and Ingman, T., Thesis, Univ. Helsinki, Finland, 1994). Sorsa, T., et al. have been able to confirm that neutrophil collagenase (MMP-8) from the PMN cells is the key member of the collagenase/MMP-group and is specifically involved in the progression of tissue destruction seen in periodontal disease (Sorsa, T., et al., J. Periodont. Res. 23, 386–393, 1988; Sorsa, T., et al., Arch. Oral. Biol. 35, 193-6, 1990; Golub, L. M., et al., J. Clin. Periodont., 22, 100–109, 1995; Sorsa, T., et al., Ann. N.Y. Acad. Sci., 732, 112–131, 1994, ingman, T., et al., J. Periodontol. 64, 82–88, 1993). Also periodontitis associated with HIV(+) infections/AIDS diseases (Robinson, P. G., et al., J. Periodont. 65, 236–243, 1994; Holmstrup, P., et al., J. Clin. Periodontol. 21, 270–280, 1994) is associated with increased amounts of activity (MMP-8) (Salo, T., et al., Ann. N.Y. Acad. Sci. 732, 476–478, 1994) Also inflammatory processes associated with peri-implantitis are known to be associated with increased activities of collagenases (MMP-8) in peri-implantitis gingival crevicular fluid (Ingman, T., et al., J. Clin. Periodontol. 21, 301–307, 1994; Teronen, O. et al., J. Dent. Res. 74, 495, 1995).

Gingival crevicular fluid and salivary collagenases (PMN MMP-8) from periodontitis patients have been found to be converted from inactive, latent proforms to catalytically active forms by periodontal inflammation (Sorsa T., et al., J. Periodont. Res. 23, 386–393, 1988; Uitto, V., et al., J. Periodont. Res. 25, 135–142, 1990). The activation of gingival crevicular fluid and salivary pro-MMPs in periodontitis could result from independent and/or co-operative action of other human/PMN-proteinases (cathepsin G), bacterial (P. gingivalis and T. denticola) proteinases and PMN-generated reactive oxygen species (such as hypochlorous acid, HOCl) (Sorsa, T., et al., N. Engl. J. Med. 321, 327–328, 1989; Sorsa, T., et al., infection and Immunity 60, 4491–95, 1992; Sorsa, T., et al., Semin. Arth. Rheum. 22, 44–53, 1992).

Collagenase activity can be measured as collagen degradation spectrophotometrically (227 nm) Lindy, S., et al., Eur. J. Biochem. 158, 1–4, 1986. The degradation of the synthetic peptide can also be monitored spectrophotometrically or fluorometrically (Tschesche, H., et al., In Methods in Enzymatic Analysis, Bergmeyer, U. H., ed., Verlag Chemie, Weinheim, Germany, pp 239–248, 1985).

With these methods, differentiation between individual collagenases is possible and can be achieved by specific inhibitors and activators (Sorsa, T., et al., Thesis Univ. Helsinki, Finland, 1989).

In general, however, the above-described methods lack the ability to distinguish between human neutrophil (MMP-8) and fibroblast-type (MMP-1) collagenase activities. Human neutrophil collagenase (MMP-8) as established by Sorsa, T., et al., (J. Periodont. Res. 23, 386–393, 1988,; Sorsa, T., et al., Arch. Oral. Biol., 365, 193S–196S, 1990) is the primary MMP in the initiation of gingival/periodontal and alveolar bone tissue destruction in periodontal diseases. Collagenases from other sources (monocyte/macrophages, epithelial cells and gingival fibroblasts) seems to exert less important roles in this context (Sorsa, T., Thesis, Univ. Helsinki, Finland, 1989; Sorsa, T., et al., Ann. N.Y. Acad. Sci. 732, 112–131, 1994; Golub, L. M., et al., J. Clin. Periodont. 22, 100–109, 1994).

Therefore, a method specific for MMP-8 in periodontitis gingival crevicular fluid would be optimal in addressing the course of tissue destruction events in periodontitis.

Collagenases can be identified by Western blotting. After SDS-PAGE and transfer onto nitrocellulose, fluoroimmunologic staining with labelled polyclonal antibodies can identify the specific enzymes.

The inventors have used polyclonal rabbit antiserum against latent and active MMP-8 in an ELISA (enzyme linked immunosorbent assay) method for quantitating total MMP-8 in gingiva crevicular fluid and saliva from patients with periodontitis and healthy controls.

However, this method is too laborious and time consuming to be used in routine laboratory work. Moreover, it is unlikely that a rapid chair-side test could be based on electrophoresis.

Gingival crevicular fluid is an inflammatory exudate that flows from inflamed human gingiva via the periodontal pocket to saliva. It reflects a myriad of inflammatory reactions occuring in the adjacent inflamed gingiva. In clinical practice, gingival crevicular fluid is easily collected by placing filter paper strips at the periodontal pocket orifice. Thus, gingival crevicular fluid is an attractive source of potential markers for the progression of periodontitis.

Biochemical marker research of periodontal disease activity has focused its attention either on gingival crevicular fluid (GCF) or on saliva/mouthrinse samples. The degradative processes in diseased inflamed human gingival tissue are reflected in adjacent gingival crevicular fluid. The advantage of gingival crevicular fluid-analysis is the site-specificity in regard to non-affected and affected sites. The disadvantage is in small sample volumes and technical difficulties in sample-collection. On the other hand, in saliva/mouth-rinse samples the concentrations of the inflammatory mediators/enzymes are often diluted and do not reflect site specificity.

As discussed above a multitude of methods for assessing periodontal disease activities have been developed. However, none of these methods are fully satisfactory. The visual examination does not allow all types and stages of periodontitis to be detected. Clinical observations are not reliable enough, because even deep pockets are not necessarily inflammatory active. Radiographic evaluations have to be combined with detailed clinical observations and visual examinations. The presence of pathogenic microorganisms do not fully reflect actual periodontic disease activity. Diagnoses based on breakdown products of have not been satisfactory either, because the presence of breakdown products may indicate rapid turnover or synthesis of collagen, not necessarily degradation thereof. Inflammatory mediators have been studied but no sufficiently rapid and specific test has been designed. Tests based on several host-derived enzymes have been developed, but they are not specific due to false positives caused by enzymes released by bacteria.

No acceptable method has been available for the MMPs. Although many biochemical methods for measuring collagenase exists, none of them have proved to be satisfactory for designing a reliable, rapid chair-side test which is a prerequisite for a successful test kit. The polyclonal antibodies which have been used are not sufficiently specific. Immunological methods such as Western blotting, ELISA and other methods discussed above require expensive instruments and facilities. They are tedious and difficult to perform. Thus, they do not provide a reliable, simple and rapid chair-side test. The state of art is discussed in McCulloch, C. A. G., J. Clin. Periodontol. 21, 497–506, 1994.

A biochemical marker test that detects periodontal disease activity in a simple, practical, and reliable manner requires sensitivity and specificity. Sensitivity is the probability that the disease is present when the test results are positive. Specificity is the probability that the disease is absent when the test results are negative. In the progression of periodontitis, an optimal test would detect all progressing periodontitis sites without registering false negative results (optimal sensitivity) and all nonprogressing sites without registering false-positive results (optimal specificity).

As addressed above, MMP-8 is directly related to the connective tissue destruction taking place during periodontitis. MMP-8 is diffused to the oral cavity through gingival pockets in gingival crevicular fluid; thus it is possible to determine site-specific periodontal disease activity by assessing the amount of activity of MMP-8 in gingival crevicular fluid samples.

ProMMP-8 is converted to the active form during inflammatory process associated with periodontal inflammation. Therefore, the determination of latent-to-active proMMP-8 conversion in gingival crevicular fluid-samples collected from periodontitis sites should serve as a specific and sensitive biochemical indicator of progressive periodontal disease activity. Western blot data done with polyclonal anti-MMP-8 from periodontally healthy and periodontitis gingival crevicular fluid samples suggest that the presence of MMP-8 indicates the presence of periodontitis with minimal false positive and negative results. However, the polyclonal anti-MMP-8 is incapable of distinguishing between active and MMP-8 and inactive proMMP-8. Therefore a test utilizing specific monoclonal antibodies to identify activated MMP-8 in gingival crevicular fluid would be optimal to screen periodontal disease activity and overcome the small size sample problem in site-specific sampling and the dilution problem in mouthrinse sampling.

Several methods have been described to measure collagenolytic enzyme activity in saliva or gingival crevicular fluid. Activity can be measured spectrophotometrically by observing the increase in absorbance caused by collagen degradation. Also, the degradation of a synthetic peptide as substrate connected to a color or fluorescence forming system can be followed spectrophotometrically or correspondingly, fluorometrically. Polyclonal rabbit antiserum reactive with both latent and active MMP-8 in an ELISA method for quantitative measurement of total MMP-8 has been used.

These methods, however, do not differentiate between MMP-8 activity which, according to the findings of the inventor is the primary cause of gingival tissue destruction in periodontal disease, and activities of collagenases from other sources. Because of involvement of various enzyme activities these methods are not specific for periodontitis and often give inflated values for reasons unrelated to periodontitis, e.g. the presence of nonpathogenic but collagenase producing bacteria.

MMP-8 (previously called collagenase/interstitial collagenase) is produced as procollagenase (proMMP-8) by human polymorphonuclear neutrophilic leucocytes (PMNs). MMP-8 is purified from PMNs as proMMP-8. ProMMP-8 is a stable polypeptide that is highly glycosylated and has a molecular weight of approximately 85,000. The proenzymes can be activated in vitro by various proteinases (e.g. trypsin, chymotrypsin and cathepsin G, but not plasmin) or by agents such as organomercurial compounds. The mechanism of activation in vivo is largely unknown but it likely occurs by reactive oxygen metabolites generated by the PMNs and oxidants (hydroxyl radical and hypochlorous acid) generated by triggered PMNs at the sites of inflammation. Activation involves cleavage of the proenzyme molecule. The cleavage creates the active collagenase. The molecular weight varies from 60,000–70,000, depending of the mode of activation (Knäuper, V., et al., Euro J. Biochem. 189, 295–300 (1990). When the N-terminal propeptides of the procollagenase is removed, the active site of the enzyme is generated and exposed. Autoactivation of proMMP-8 can also occur with no molecular splitting (Saari, H., et al., Biochem. Biophys. Res. Commun. 171, 979–987, 1990).

THE SUMMARY OF THE INVENTION

As discussed above various host-cell derived inflammatory mediators are produced by periodontal tissues in gingivitis, periodontitis, peri-implantitis and HIV(+)-infection/AiDS-related periodontal diseases. The conjuncture that some of these host cell derived inflammatory mediators could be central in the tissue destruction in periodontitis led the inventors to examine the possibility that one or more of these inflammatory mediators would be useful as a biochemical marker for progressing lesions.

The inventors have now found that monoclonal antibodies that recognise the active form of mammalian MMP-8 and differentiate between the active and proenzyme forms provide the means for constructing reliable and sensitive methods and test kits for diagnosing periodontitis. It is the enzymatically active site that all the different molecular forms of active MMP-8 share and therefore, antibodies that are intended to be used in detecting active MMP-8 are developed to recognize this site. The antibodies must bind to the active site similarly and regardless of the size of the rest of the molecule.

Accordingly, the present invention provides methods for a reliable, reproducible, sensitive and specific diagnosis of periodontal disease activity based on monoclonal antibodies which can recognize the active mammalian matrix metalloproteinase 8.

The invention also provides methods which can be used chair-side, and which, in addition to specificity, sensitivity and reliability, are rapid and easy to perform. These chair-side methods do not require elaborate equipment and facilities. The sampling is non-traumatic. The methods of the present invention are useful four site-specific sampling and simplified prescreening procedures.

The invention also provides methods which overcome the dilution problems related to mouth-rinse sampling and the small size of site-specific samples.

The present invention also provides means for an early and reliable diagnosis of peri-implantitis as well as means to diagnose and to monitor the course and progression of gingivitis and periodontal diseases associated with HIV(+)-infections/AIDS disease.

The methods of the present invention can be practiced by assembling of the test kits. The methods of the present invention can be practiced by means of the test kits assembled for chair-side diagnosis.

The test kits according to the invention comprises at least one monoclonal antibody which recognizes an active mammalian MMP-8 produced by PMN.

The test kit of the present invention optionally contains other monoclonal antibodies, which recognize, but do not differentiate between the inactive and active mammalian MMP-8 and can be used in optional test kit constructions.

The test kit may also contain direct or indirect label(s) as well as optional solid or liquid carriers for performing immunological tests.

The present invention is related to a test kit for diagnosing periodontal disease activities. The test kits according to the invention comprise at least one monoclonal antibody which recognizes an active mammalian, especially the human matrix metalloproteinase 8 (MMP-8) produced by polymorphonuclear neutrophilic leucocytes (PMN).

The test kit may also contain the direct or indirect label(s), which are detectable as well as the optional solid or liquid carriers which are needed for performing the immunological tests.

Any of the well-known immunological assays are applicable. In a preferred embodiment, immunochromatographic methods based on the lateral flow-principle and immunochemical, especially immunometric methods based on the flow-through principle are used.

Antibodies that recognize the active and inactive forms of MMP-8 are monoclonal. However, the invention also includes polyclonal antibodies having the required characteristics which can be used in addition to the monoclonal antibodies. Antibodies can be derived from any mammalian source. Antibodies are understood to recognize MMP-8 from any mammalian source.

The monoclonal antibodies, which recognize the active mammalian MMP-8 are monoclonal antibodies obtainable by a method in which the inactive mammalian and/or human MMP-8 is activated and the immunization is performed with a mixture of different isoforms of actired MMP-8. Cell lines are produced by conventional hybridoma techniques followed by screening for cell lines that produce the different types of monoclonal antibodies required in the test kits and methods of the present invention.

The present invention also relates to methods for diagnosing periodontal disease activity. The methods are performed as immunological assays, which comprise the steps of collecting a sample and contacting the sample with a monoclonal antibody or monoclonal antibodies that recognize only an active mammalian MMP-8, and simultaneously or after that step contacting the sample with an additional antibody or antibodies which can be monoclonal or polyclonal that recognize the inactive mammalian proMMP-8. These antibodies may be incorporated in the test kits in an appropriate way and the test performed by using detection methods which allow an easily interpretation of the results.

Samples are collected preferably in a site-specific manner from gingival crevicular fluid associated with a specific site or lesion.

In a further embodiment of the present invention the risk for periodontitis is prescreened by testing a salivary sample or a mouthrinse sample. Positive cases are followed up by site-specific methods, wherein the collecting of the sample is performed with a solid, absorbing sampling device, which might or might not act as the immunological test strip.

THE DETAILED DESCRIPTION OF THE INVENTION

In the following description, reference will be made to various methodologies known to those skilled in the art of immunology and immunopathology, clinical chemistry, pharmaceutical sciences and dentistry and dental pathology. Publications and other material setting forth such known methodologies to which reference is made are incorporated herein by reference in their entireties as though set forth in full.

General principles of immunoassays and the generation and use of antibodies as laboratory and clinical tools are set forth, for example, in Antibodies, A Laboratory Manual (Harlow, E. and Lane, D., eds., Cold Spring Harbor Laboratory, Cold Spring Harbor, N.Y., 1988).

General principles of pharmaceutical science are set forth, e.g., in Remington's Pharmaceutical Sciences (18th edition, Gennaro, A. R., ed., Mack Publishing, Easton, Pa. 1990).

DEFINITIONS

Unless defined otherwise, all technical and scientific terms used herein have the same meaning as is commonly understood by one skilled in the art to which this invention belongs. In the description as follows, a number of terms used in immunology and dentistry are extensively used. In order to provide a clear and consistent understanding of the specification and claims, including the scope to be given such terms, the following definitions are provided.

"Antigen" refers to any composition, organism, or material, that is capable of eliciting an antibody response specific for that composition, organism, or material.

"Chair-side test" refers to a test or procedure which may be performed while the patient is in the dental office, as in the dental operatory, by dental office personnel.

"Periodontal disease" refers to a disease of the supporting structures of the teeth, or the periodontium, which typically includes both soft tissue inflammation and loss of alveolar bone support. It also includes peri-implantitis and HIV(+)-infection/AIDS-disease related periodontal diseases.

"Gingivitis" refers to a condition wherein the gingivae, or attached mucosal soft tissues of the mouth, are in a state of inflammation.

"Metalloproteinase" refers to the family of collagenases that include human polymorphonuclear leukocyte (PMN) collagenase MMP-8 and human fibroblast collagenase MMP-1. MMP-8 is the primary metalloproteinase associated with the initiation of gingival and periodontal disease. Metalloproteinases are synthesized by either bacterial or mammalian cells. They are initially synthesized in an inactive, or "proenzyme" form and become enzymatically active if they are cleaved to create or expose the enzyme's active site. The generation of the active site may be effected by chemical or enzymatic cleavage of the proenzyme either in vivo or in vitro. In vivo, enzymes are capable of generating the active site and may be of bacterial or endogenous, i.e. mammalian origin. The proenzyme may also be referred to as the "proform".

"Isoform" refers to the different forms of the same protein. For example, active collagenases as metalloproteinase MMP-8, are generated by the cleavage of the proenzyme to form an active enzyme with an exposed active site, as noted above. Different reactions, including different enzymatic reactions, are capable of creating an active enzyme. These varied reactions cleave the proenzyme differently, generating different molecular species called isoforms. In the present invention the antibodies which recognize the proenzyme are preferably recognize the part of the enzyme which is common to the active and inactive form of the enzyme.

"Peri-implantitis" refers to the state of soft and bony tissue inflammation effected by stable implants which have been surgically implanted into the alveolar bony ridge.

"Site-specific sampling" refers to a method or procedure wherein the material to be sampled solely in a distal periodontal lesion to effect the testing of intracrevicular fluid only from the distal periodontal pocket.

"Direct label" refers to a label that allows detection of an antibody or an antigen in an assay wherein the detectable label is directly attached to antibody or antigen taking part in the principal immunoreaction.

"Indirect label" refers to any label that allows detection of an antibody or antigen in an assay wherein the detectable label is not directly attached to the antigen or antibody taken part in the principal immunoreaction but is added to the reaction to mixture to indicate that the immunoreaction has occured.

"Solid carrier" refers to a solid medium or solid phase to which an antibody is attached. For example, when proteins such as antibodies are attached to latex beads, colloidal metal, polyvinylchloride (PVC) and polystyrene. *Staohylococcus aureus* Protein A or nitrocellulose membranes, those proteins are attached to solid carriers.

"Liquid carrier" refers to a liquid medium or liquid phase that is capable of effecting the movement of a composition, such as an antibody or antibody-conjugate complex, wherein the composition diffuses with the liquid.

"Immunoassay" refers to a method or procedure capable of detecting and/or measuring a substance wherein the active and specific reagents include at least one antibody capable of specifically binding said substance. Basic types of immunoassays include antigen capture assay, antibody capture assay and antibody sandwich assays which are defined below.

"Two Antibody Sandwich Assay" refers to an immunoassay capable of detecting or quantitating the amount of antibody or antigen in a sample. The assay requires: the use of two different antibodies capable of binding two different, non-overlapping (noncompetitive) epitopes on an antigen.

"Lateral Flow Technique" refers to an immunoassay using immunochromatographic principles. It is typical for the test that the sample or test solution which is in liquid form moves along a test strip in contrast to the "Flow-Through Technique" in which the test solution is allowed to flow through a membrane in a test device.

"Flow Through Technique" is an immunoassay often based on the sandwich technique. The antigen containing sample or test solution is applied as a spot and is allowed to diffuse through a membrane in device. "RIA" or "radioimmunoassay" refers to immunoassays wherein the detectable label is a radiolabel in the form of a radioisotope attached to an antigen.

"IRMA" or "immunoradiometric assay" refers to an immunoassay wherein the detectable label is a radiolabel in the form of a radioisotope attached to an antibody.

"Enzyme immunoassay" refers to any immunoassay which includes the use of enzymes as active reagents. For example, the enzyme may be attached to a primary or secondary antibody. The enzyme may react with a chromogenic substrate.

"Fluoroimmmunoassays" refers to any immunoassay which include the use of fluorescent substances as detectable labels.

"Luminescence immunoassays" refers to any immunoassay which includes the use of luminescent substances as detectable labels.

"Immunoagglutination assays" refers to any immunoassay which uses agglutination of particles by multivalent antigens as the means of detecting an immunospecific reaction. For example, when purified antibodies are attached to red blood cells or coloured beads and multivalent antigens reactive with said antibodies are added to the immunospecific antibody/antigen reaction leads to aggregation, or agglutination, of said particles.

"Turbidimetric immunoassay" refers to any immunoassay which uses the measurement of turbidity of particles by multivalent antigens as the means of detecting an immunospecific reaction. For example, aggregation of antibody-conjugated particles by multivalent antigens and optionally further enforced by using microparticles may create a measurable turbidity to an otherwise clear solution.

"Nephelometric immunoassay" refers to a variant of the "Turbidimetric immunoassay".

The invention relates to biochemical means and methods, especially immunological means and methods for diagnosing and assessing progression of periodontal disease. The methods and means apply to mammals, particularly, humans. The means and methods provide a reliable chairside test. The methods and test kits of the present invention are also applicable for assessing peri-implantitis as well as HIV(+)infection/AIDS-disease related periodontal diseases.

The invention relates to test kits providing means to practice the methods of the invention using antibodies to diagnose periodontal disease. The test kit according to the present invention may contain several antibodies but must contain at least one monoclonal antibody which recognizes an active mammalian, preferably a human MMP-8 and at least one label. The label may be attached to the antibody. The test kit may also provide means for differentiating between active MMP-8 and inactive proMMP-8. It is to be understood that the mammalian MMP-8 and proMMP-8 encompasses MMP-8 and pro-MMP8 from any given mammal. However, it should be recognized that human is the most preferable species. Of course, domestic and veterinary animals are also included.

The antibody of the invention is preferably monoclonal, especially the antibody that recognizes active MMP-8. However, any antibody having the requisite characteristic, as described herein, is included.

The monoclonal antibody that recognizes the active mammalian MMP-8 is obtainable by a method which comprises the following steps. inactive mammalian proMMP-8 in either a crude or highly purified preparation is activated. Activation can occur by autoactivation. Preferably, activation is in vitro including, but is not limited to, activation by enzymes such as trypsin, chymotrypsin, or cathepsin G. Chemical agents such as organomercurial compounds and/or oxidating agents such as NaOCl can also be used. These substances can be used separately or in combination. Different activation methods can also be used on the same sample.

After the activation, mice are immunized with a mixture of different isoforms of the active mammalian MMP-8. Hybridoma cell lines are produced by conventional hybridoma techniques and screened for different types of monoclonal antibodies. The most desired monoclonal antibodies recognize only the active mammalian MMP-8. They are sensitive (of sufficient affinity) and they have a minimal cross-reaction with inactive proMMP-8 and other structurally related enzymes (of sufficient specificity).

Monoclonal antibodies having essentially the same properties obtainable by essentially the method described above or obtainable by conventional methods for preparing monoclonal antibodies are within the scope of this invention. The phage display method described for example in the patent publications WO 90/14443 and WO 92/18619, which are hereby incorporated by reference can also be used.

The test kit of the present invention can, in addition to the monoclonal antibody recognizing the active mammalian MMP-8 contain at least one second monoclonal antibody which cross-reacts with the inactive mammalian proMMP-8. The antibodies can be polyclonal or monoclonal, but are preferably monoclonal. When monoclonal, they are obtainable by using conventional hybridoma techniques or by a technique essentially the same as above but also using other screening criteria.

Different types of test kits can be constructed to suit the immunological method which has been selected. Carrier materials and accessories are included in the test kit depending upon the method desired. The method is preferably chosen among immunochromatographic methods, immunometric methods, radioimmunoassays, radioimmunometric assays, enzyme immunoassays, fluoroimmunoassays, luminescence immunoassays, immunoagglutination methods, hemagglutination methods, inhibition of agglutination methods and turbidimetric immunoassays. The detectable labels and optional carriers are selected according to the appropriate method.

The most preferred test kits of the present invention for chair-side use are constructed according to immunochromatographic methods based on the lateral flow principle or an immunometric method based on the flow-through principle.

In addition to the antibody which recognizes active mammalian MMP-8, the test kit can contain an optional second antibody, which recognizes an inactive mammalian proMMP-8. This second antibody is also preferably labeled with at least one detectable label selected from a group consisting of direct or indirect labels. The second antibody can be monoclonal or polyclonal. The second antibody need not differentiate between the proMMP-8 and active MMP-8. In other words, the test kit according to the present invention may in addition to the monoclonal antibody which recognizes the active mammalian MMP-8 contain at least one second antibody.

The method for diagnosing periodontal disease activity, is essentially performed as an immunological assay including the following steps. Gingival crevicular fluid sample is collected with a sampling device. Simple solid devices can be used for collecting site-specific samples. In an optional embodiment of the invention the sampling device is also used as the test device. The sample is then contacted with at least one monoclonal antibody, which is already attached to the sampling or test device or can be added to the combined sampling and test device. Alternatively, the sampling device can be added to the test device, which contains the monoclonal antibody.

The detection of MMP-8 is preferably performed by the aid of an immunological method capable of differentiating between the active MMP-8 and inactive proMMP-8.

In a preferred method, periodontal disease activity is detected by a site-specific method in which the sample is collected with a solid, absorbing sampling device which can act as a test device.

According to one embodiment the risk for periodontal disease activity can be prescreened by testing for an increased level of MMP-8 in a salivary sample or a mouthrinse sample. The prescreening activity can be performed as an immunological assay using the following steps. A sample containing gingival crevicular fluid is collected and the sample is then contacted with at least one antibody, which recognizes MMP-8. An increased level of MMP-8 is detected by an immunological method.

The invention also encompasses a set of test kits for chair-side diagnosis. In each test kit at least one monoclonal antibody which recognizes the active mammalian MMP-8.

The set may be provided in a packaged combination containing one or more prescreening test kits and one or more mouthrinse vials and one or more site-specific test kits, which in addition to the monoclonal antibody contains one or more sampling devices. These prescreening and site-specific test kits can be provided in combinations of variable numbers which allow the prescreening of e.g. all children in a school class and site-specific confirmation tests of those who have an increased level of MMP-8.

The methods and materials used to develop the test kits and the methods of the present invention are discussed in more detail below.

Collagenolytic enzyme activities in saliva and in gingival crevicular fluid can be assessed by various known methods. The inventors have been able to estimate the amount of latent proMMP-8 and active MMP-8 in saliva and gingival crevicular fluid from adult periodontitis patients and periodontally healthy individuals by ELISA, SDS-PAGE, and Western blot.

Different collagenases have also been identified by Western blotting; that is: after SDS-PAGE of the enzyme preparations the bands have been transferred onto nitrocellulose and characterized by fluoroimmunologic staining with labelled polyclonal antibodies to MMP-8, MMP-1 and other enzymes to be studied.

With methods like this, a more specific result in regard to actual cellular source and degree of activation of collagenase/MMPs is obtained, but they are far too laborious and time consuming to be used in routine laboratory work. Moreover, it is impossible that a rapid chair-side test would be based on any kind of electrophoresis.

Connecting the results of his studies the inventor Dr. Timo Sorsa was able to estimate the amounts of latent and active MMP-8 in saliva and gingival crevicular fluid from adult periodontitis patients and periodontally healthy individuals. Concentration data of saliva and gingival crevicular fluid from adult periodontitis patients and periodontally healthy controls in an ELISA assay was interpreted together with SDS-PAGE/functional assay and Western blot data.

In the first preliminary tests it was shown that if the level of MMP-8 is at least 1 µg/ml in case of a direct site-specific sampling of gingival crevicular fluid there is a risk for periodontal disease activity or peri-implantitis. In a salivary sample about 2 µg/ml indicates a risk (Table 1 below).

In later performed ELISA tests (Lauhio, A., et al., Antimikrobial. Agents Chemother. 38, 400–402, Lauhio, A., et al., Clin. Exp. Immunol. 98, 21–28, 1994) with sensitive, reliable and specific antibodies it was found (Table 2) that, if the level of total MMP-8 in a direct site specific sample is above 100 ng/ml there is a risk for periodontal disease. In a salivary sample the corresponding risk level is 200 ng/ml. In actively progressing periontitis the corresponding risk levels of active MMP-8 are about 1000 ng/ml in a site specific sample and about 200 ng/ml in a salivary sample.

In the preliminary tests (Table 1) it was estimated that gingival crevicular fluid from adult periodontitis patients contained about 1.1–3.6 µg/ml of total and 1.0–1.5 µg/ml active MMP-8, respectively. In the same preliminary test the gingival crevicular fluid of healthy subjects contained 0.02–0.08 µg/ml of total and less than 0.05 µg/ml of active MMP-8, respectively.

Table 2, below, shows salivary MMP-8 values obtained with ELISA-tests. These results clearly indicate that MMP-8 is an optimal marker for diagnosing and assessing progress of periodontal disease activity. However, the actual ELISA-values obtained seem to vary due to variations in antibody specificities, sampling techniques and the sampling time. Reliable threshold values are however obtainable from these results. These threshold values allow the designation of reliable test kits.

The different numeric results reflect the use of different sets of antibodies as well as other variation in the test conditions. However, it is important to notice that for the active MMP-8 the ratio between diseased and healthy persons remains approximately the same. These findings indicate that a immunochromatographic test using monoclonal antibodies which differentiate between the latent and active MMP-8 would be optional for diagnosing periodontal disease activity.

TABLE 1

The first preliminary tests showing tissue destructive human neutrophil collagenase (PMN MMP-8) in gingival crevicular fluid (GCF) and saliva from untreated adult periodontitis patients (n = 15) and periodontally healthy individuals (n = 15) as determined by MMP-8 specific ELISA-techniques

| Patient group | Oral fluid | MMP-8 concentration (µg/ml) | |
|---|---|---|---|
| | | Active | Total |
| Healthy controls | GCF | <0.05 | 0.2–0.8 |
| Healthy controls | saliva | 1–3 | 1.2–3.4 |
| Adult periodontitis | GCF | 1,0–1,5 | 1,1–3,6 |
| Adult periodontitis | saliva | 2–6 | 3–8 |

TABLE 2

Tissue destructive human neutrophil collagenase (PMN MMP-8) in gingival crevicular fluid (GCF) and saliva from untreated adult periodontitis patients (n = 15) and periodontally healthy individuals (n = 15) as determined by MMP-8 specific ELISA techniques.

| Patient group | Oral fluid | MMP-8 concentration (ng/ml) | |
|---|---|---|---|
| | | Active | Total |
| Healthy controls | GCF | <0.05 | 10–20 |
| Healthy controls | saliva | 3 | 30–50 |
| Adult periodontitis | GCF | 800–1600 | 1500–3000 |
| Adult periodontitis | saliva | 200–300 | 400–600 |

Western blot analysis using both anti-human MMP-8 and anti-human MMP-1 from the sample material given in Table 1 show that MMP-8 existed in 70–75 kD inactive or latent and 65 kD active forms, and MMP-1 was not detected. MMP-1 was not detected by specific ELISA recordings either.

The findings of the inventors (Table 2) are in agreement with recent results of Haerian, et al., (J. Dent. Res. 73, 208, 1993) showing gingival crevicular fluid from periodontitis patients containing increased amounts of functionally assessed MMP-8 but hardly any immunoreactive fibroblast-type MMP-1. The origin of collagenase activity was ascertained to be MMP-8 by Western-blotting (Sorsa, T., et al., Ann. N.Y. Acad. Sci. 732, 112–131, 1994) MMP-1 was not detected in gingival crevicular fluid obtained from periodontally healthy controls (Table 1).

It has also been found that MMP-8 plays a central role in peri-implantitis (Teronen, O., et al., J. Dent. Res. 74, 495, 1995) and, in addition, increased amounts of active MMP-8 have recently been detected in gingival crevicular fluid collected form periodontitis sites/pockets of HIV(+)/AIDS-patients (Salo, T., et al., Ann. N.Y. Acad. Sci. 1732, 470–478, 1994). This is a type of inflammation in the connective tissues surrounding dental implants (Ingman, T., et al., J. Clin. Periodontal. 21, 301–307, 1994; Teronen, O., et al., J. Dent. Res. 74, 495, 1995) and HIV(+)-infection and AIDS-related periodontal diseases (Robinson, P. G., et al., J. Periodontal. 65, 236–242, 1994; Holmstrup, P., et al., J. Clin. Period. 21, 270–280, 1994) has been described recently.

MMP-1 was not detected in gingival crevicular fluid from the corresponding samples from adult periodontitis patients and healthy controls.

The degradation of connective tissue macromolecules during peri-implantitis has been found to be mediated by human matrix metalloproteinases, especially neutrophil (PMN)-derived matrix metalloproteinase (Sorsa, T., et al., Ann. N.Y. Acad. Sci. 732, 112–131, 1994; Teronen, O.,m et al., J. Dent. Res. 74, 495, 1995). Thus, it is possible to assess peri-implantitis by the test-kit and method of the present invention.

Monoclonal antibodies against active MMP-8

The exposed enzymatically active site is common to all the different molecular forms of active MMP-8 and the present invention is based on an immunochemical test capable of recognising said active site. The specificity, which is required in the test according to the present invention is achieved by using monoclonal antibodies that are specifically targeted to the active site. These monoclonal antibodies are able to bind epitopes on the active site regardless of the size of the rest of the molecule.

Monoclonal antibodies of the present invention are developed according to the original technique of Köhler and Milstein (Nature 256, 495, 1975). The inventors have used the specific application thereof published by Stenman U., et al. (J. Immunol. Meth. 46, 337, 1981).

Developing Antibodies

The molecular configuration of active MMP-8 may differ from individual to individual. In vivo, activation of the proenzyme proMMP-8 may occur by different host intracellular factors but also by certain bacterial proteases from putative periodontopathogens. The bacterial species and bacterial proteases found in individuals also varies from patient to patient. Experimental in vitro activation methods may produce active MMP-8 isoforms that exist in patient tissues very rarely or not at all.

This variation in isoform molecular configuration is taken into account in the procedure of developing monoclonal antibodies for the present invention. If mice are immunized with only one active isoform and the same isoform is used in screening, antibodies reactive with only this isoform could result. False negative results would occur in patients with the other isoforms if only this single antibody is used. Thus, this invention incorporates the use of antibodies capable of recognizing all active isoforms.

In the present invention, immunization scheme uses different molecular isoforms of active MMP-8 as immunogens to allow selection for antibodies reactive with common epitopes, as the active site, for example. The crucial point, however, is the system to test hybridomas and clones. Hybridomas are screened with one isoform that occurs widely in patients. The clones developed are further tested against various types of active MMP-8 before the final choice of a broadly reactive antibody.

Antigen used for immunisation

The ideal antibodies recognize the active site of MMP-8 equally well in all possible molecular configurations (isoforms) of the active enzyme. In immunization, a crude preparation of MMP-8 is initially used, but in the last booster the presence of different active molecular forms is ensured by using a mixture of highly purified, active MMP-8 preparations. MMP-8 is activated in vitro by, for example, three different techniques. This results in an optimal variety of active site-specific antibody producing hybridomas. Those not recognizing the rest of the molecule can be selected.

Proenzyme proMMP-8 is partially purified from human PMN leucocytes in buffy coats (Sorsa, T., Scand. J. Rheumatol 16, 167–175, 1987; Knäuper, V., et al., Eur. J. Biochem. 189, 295–300, 1990). For the last booster, the antigen is further purified and used as a mixture (for example, 1:1:1 molar ratios) of isoforms activated by, for example 1) autoactivation, 2) treating with an oxidant and 3) enzymatic degradation with a human and bacterial proteinase (for human cathepsin G: Saari, H., et al., Biochem. Biophys. Res. Commun. 171, 979–987, 1990; T. denticola chymotrypsin-like protease: Sorsa, T., et al., Infection and Immunity 60, 4491–95, 1992). Alternatively, individual mice can be boosted with one isoform.

Autoactivation of the MMP-8 preparation is performed as published (Sorsa T., Thesis, Univ. Helsinki, Finland 1989). For oxidant activation, NaOCl is employed as the oxidating agent and activation is performed essentially as described (Saari, H., et al., (Biochem. Biophys. Res. Commun. 171, 979–987, 1990). The method of Sorsa, T., et al. (Infection and Immunity 60, 4491–95, 1992) is used for activation with a proteinase obtained from human neutrophils and T. denticola. Immunisation, fusion, cloning and transplantation of clones BALB/c mice are immunized and boosted intraperitoneally with 300–500µl of a solution containing 50–100 µg/ml of crude active MMP-8. This is done by injection in Freund's incomplete adjuvant at 2–4 week intervals. If the mice have an antibody titer after the first boost they are boosted intravenously with 50–100 µg of the antigen mixture described above in saline. The spleen is removed 3–4 days after the last booster. $1-2 \times 10^8$ spleen cells are fused in polyethylene glycol (PEG, Boehringer Mannheim Cat. no. 1243268) with $2.5-5.0 \times 10^7$ P3×63-Ag8.653 myeloma cells (Syngeneic) in exponential growth phase. After fusion, cells are plated into U-bottomed microplates in Dulbecco's modified Eagle's medium (DME) with 15% horse serum or RPMT-1640 with 7.5% horse serum at a density of $2 \times 10^6$ cells/ml. Each well contains 0.1 ml of culture medium. After 1 day, 0.1 ml of selective HAT medium (2% mixture of hypoxanthine, aminopterin and thymidine in DMEM, Gibco 50× HAT, Cat. No. 043-01060H) is added to the cultures. After this, half of the medium is removed every other day and replaced with fresh HAT medium.

After 2 weeks of culture the cells are transferred to HT culture medium (2% HAT without aminopterin, Gibco 50× HT, Cat. no. 043-01065H), which is changed three times a week for two weeks. After 2 weeks the culture medium is replaced with DME+15% horse serum or RPMT-1640 and 7.5% horse serum. Vigorously growing antibody-producing cultures are screened and characterized as described. The cultures of selected hybridomas are then cloned by limiting dilution in flat-bottomed microtiter plates on human fibroblast feeders. Antibody-producing clones are recloned in 96 well plates. Subclones are expanded in test tubes and later in Falcon tissue culture flasks.

For transplantation of the hybrid clones, antibody-producing cells ($1 \times 10^6$/animal) are injected intraperitoneally into BALB/c recipients primed with pristane (2,6,10,14-tetramethylpentadecane, Aldrich). Ascites developes within 3–4 weeks. The ascitic fluid is withdrawn and the antibody in the fluid tested.

Screening and titration

The supernatants from the cultures are screened for antibody production at weekly intervals from hybridization or cloning. Titrations of the antibodies are performed weekly. Antibody titration is also carried out on antisera from immunized mice and in ascites fluid.

To detect antibody production against the active site of said MMP-8, a radioimmunoassay (RIA) is used. Radioiodinated activated, highly purified MMP-8 is used. For activation, degradation of MMP-8 with human PMN cathepsin-G can be used. PMN cathepsin-G may serve the endogenous proteolytic proenzyme proMMP-8 activator (Suomalainen, K., Thesis, Univ. Helsinki, Finland 1993).

ProMMP-8 is activated by PMN cathepsin-G by a proteolytic action at the proMMP-8 N-terminus by splitting the $Phe_{79}Met_{80}$-peptide. This results in the conversion of 85 kD inactive proMMP-8 to 64 kD active form of MMP-8. A corresponding split at the prOMMP-8 N-terminus has been found by the inventors to be related to the activation of proMMP-8 by T. denticola chymotrypsin-like proteinase. Cathepsin-G activated MMP-8 is radioiodinated with a Chloramine T method (Greenwood, F. C., et al., Biochem. J. 89, 114, 1963) and used as a label in the screening assay. In the assay, 50 µl of supernatant is incubated with 150 µl of the $^{125}$I-label of antigen (about 10,000 cpm) in a phosphate-EDTA-NaCl buffer containing 0.33% BSA, pH 7.4. After overnight incubation, bound label is precipitated by the addition of 100 µl of bovine gammaglobulin (IgG) in phosphate buffer and 1 ml of 20% PEG 6000 in phosphate buffer. After centrifugation, the supernatant is aspirated and the radioactivity of the precipitate is counted. A sample is considered positive for antibody production when the activity precipitated is significantly greater than the background (growth medium instead of culture supernatant), i.e. bound activity is more than 50% of the maximal binding of the polyclonal preparation used as a control.

When titrating, the titer is defined as the dilution binding 50% of the maximal amount of label specifically bound by a large excess of antibody. Polyclonal antiMMP-8 recognizing both inactive proenzyme and active MMP-8 is used as control antibody.

Methods of testing and characterization

The positive hybridoma cultures are further tested for their sensitivity to detect active MMP-8, i.e. their reactivity with active MMP-8 and for their cross-reaction with the proenzyme. An RIA method is used. The label is the same preparation of radioiodinated cathepsin G-activated MMP-8 described above in the screening assay. 100 µl of label, 50 µl of standard or the cross-reactant to be tested and 50 µl of antibody solution (all in phosphate-EDTA-NaCl buffer containing 0.33% BSA, pH 7.4) are incubated overnight. Separation of bound radioactivity is performed similarly to the screening method. Each antibody is diluted to bind about 50% of its maximal binding capacity. Standards are prepared from cathepsin-G activated MMP-8 in concentrations ranging 10–1000 µg/l.

The hybridomas with best sensitivity and with no cross-reaction with proMMP-8 are selected to be cloned. The specificities of the new monoclones are further characterized. Anti-bodies secreted by these clones are assayed by RIA for binding of the 3 MMP-8 isoforms used in immunization. For use in the diagnostic test, clones are selected that react with all the isoforms. The epitope common to all the isoforms may be the enzyme active site. The clones are also tested for their cross-reaction to enzymes structurally and immunologically related to MMP-8 which may be present in gingival crevicular fluid samples (e.g., PMN-gelatinase [MMP-9], fibroblast type collagenase [MMP-1] and stromelysin-1 [MMP-3]) Clones producing cross-reactions >0.01% (defined as percentage of the cross-reactant concentration of standard concentration that will cause a 50% displacement of the label) are not selected. The immunoglobulin isotype produced by the selected clones is determined by a kit method (Mouse Typer, BioRad, California). The antibodies are purified by affinity chromatogaphy with Protein A (Pharmacia, Sweden) and their isoelectric points are recorded by isoelectric focusing (Phast System, Pharmacia, Sweden) using standard techniques.

Monoclonal antibodies against PMN procollagenase (proMMP-8)

Some immunoassays, especially the immunometric method requires two different antibodies, i.e. an antibody pair which can bind simultaneously to the same antigen molecule. Therefore, the antibodies must recognize different epitopes of the molecule and those epitopes must be distant enough that binding occurs without steric hindrance causing loss of affinity. In active MMP-8 the active site is not large enough to accommodate two antibodies. However, binding simultaneously it is sufficient if only one of the antibodies is specific. The other antibodies recognize an epitope that is situated in that part of the MMP-8 molecule that is common to all active and inactive forms.

To select the second antibody, hybridomas showing a strong cross-reaction with proenzyme are selected to be cloned. Among these clones, those are finally selected that have the broadest specificity to both active and inactive forms. In a test for measuring total collagenase enzyme (active MMP-8 and inactive prOMMP-8 simultaneously) two of monoclonal antibodies selected—one specific for the active enzyme and one able to react with the part of the enzyme which is common to the active enzyme and the proenzyme.

Diagnostic test methods for determining periodontal disease activity

The monoclonal antibodies specific to active human and/or mammalian MMP-8 developed according to the above procedure are used for designing a variety of test methods useful in the assessment of periodontal disease activity. Quantitative and qualitative methods are described below.

A standard method for immunologically detecting the presence of an antigen is visually observing agglutination of antibody-coated particles caused by antigen binding. The particles include latex particles. Part of the latex particles are coated with monoclonal antibodies specific to the active site of MMP-8 and part are coated with antibodies specific to an epitope outside the active site. When active MMP-8 is present the two kinds of particles are bound in a network via antigen bridging and thus agglutination occurs. Red blood cell can be used as particles if a so-called hemagglutination test is provided. Inversely, the principle of inhibition of agglutination can be used.

A more recent method involves the use two antibodies in a flow-through immunometric technique (U.S. Pat. No. 4,366,241). The test is best performed in a device wherein a pad of absorbing material is covered by a membrane of, for example nitrocellulose or nylon. On the membrane is an area on which antibodies of one kind (for instance, those recognizing the active site of MMP-8) are attached. Liquid sample is pipetted on the membrane and any active MMP-8 present in the sample will be bound to the antibodies. The rest of the sample will flow through the membrane. Then, a labeled reagent is added. This label can be a conjugate of the second antibody (monoclonal or polyclonal antiMMP-8 recognizing an epitope other than the first antibody) and an enzyme like horseradish peroxidase. If there is any MMP-8 bound on the membrane the conjugate will bind to it and can be visualized by washing off excess conjugate and adding a precipitating substrate to the labeled enzyme. The precipitated substrate can produce a visible color. The substrate can also be one producing an invisible signal, for example a fluorescence or chemiluminescence signal. Intensity of colour, fluorescence or chemiluminescence can be recorded by appropriate instruments and in these cases, if concentration calibration is used, the test result can be quantitated. The labeled reagent can also be a suspension of colored (or otherwise signal producing) particles (made of, for example, latex) that are coated with the second antibody. Here, the pore size of the membrane is so adjusted that those particles that are not immunochemically bound on the membrane will flow through the pores. After a washing step, the bound particles can be detected directly if visual or indirectly by signal measurement.

The periodontal disease activity test as described herein can be based on the immunochromatographic principle. This technique, often referred to as the lateral flow technique, has been described in detail in EP 291 194 which is incorporated herein by reference. WO 94/15215 includes a test device that essentially consists of a membrane and an absorbing pad in a dipstick constructed with a chamber-like gap. In the immunometric version that employes two different antibodies, the first antibody (i.e. recognizing the active site of the MMP-8) is coated on particles that act as a label detectable by eye (color visible) or by suitable instruments (fluorescent or chemiluminescent signal producing). The particles can be made, for example, of latex, colloidal metal (gold, selene) or a dispersing dye. These label particles are attached in a test device so that when the absorbing part of the device is brought into contact with the liquid sample and the sample is absorbed, the particles will migrate with the liquid flow and simultaneously, label antibody will bind the antigen (active MMP-8) if present in the sample. The liquid will be further absorbed into the membrane in the device. On the membrane, a second antibody (monoclonal or polyclonal antiMMP-8 recognizing an epitope other than the first antibody) has been attached in a zone-like area. When the liquid flow carrying the label migrates through this zone, those label particles that have bound antigen will be bound to the zone. Thus, the zone will be detectable if there was antigen present in the sample.

This immunoassay technique can also be based on the use of one antibody only. This can be done by using antigen coated label particles in competition with antigen possibly present in the sample. The monoclonal antibody specific to the active site of MMP-8 is attached in a zone on the membrane. Sample antigen will occupy the antibody binding sites in the zone and thus, no detectable zone will appear. In another version, labeled particles coated with an antigen analogue are loosely bound to the antibody attached in the absorbing area. Sample antigen will displace the analogue in antibody binding and label particles are able to migrate to a zone containing a capture reagent.

Immunochromatography can also be made quantitative by measuring the signal produced by a label that is bound to the membrane when known standards or unknown samples are run. Visual semiquantitation is possible if several antibody zones with increasing antibody amount in the zone are used in the test device.

The above mentioned immunoassay techniques are useful for the development of a rapid chair-side test with a short performance time (often only a few minutes). The more recent techniques (lateral flow and flow-through) will provide tests that can be performed and interpreted very reliably by personnel untrained to laboratory work. They also lack some major disadvantages connected with agglutination methods, such as, for instance, false positives with samples containing rheumatic factor and difficult interpretation of, especially, turbid samples.

However, other immunological methodologies can be adapted in a test for assessing periodontal disease activity. These methods are usually performed in a laboratory because of the need for specific, possibly automated, instrumentation and/or trained personnel. The following techniques are also suitable if a quantitative test result is required. Turbidimetric and nephelometric methods can be used. They usually employ polyclonal antibodies, but in an assay like this where specificity based on monoclonal antibodies is needed, the reagents used consist of a mixture of latex particles of suitable size coated with two different antibodies. Classical immunochemical methodologies with radioisotopic labels can be applied (radioimmunoassay involving one antibody in a competitive assay design, and immunoradiometry involving an antibody pair). instead of isotopic labels, a variety of other labeling compounds are useful in related immunoassay methodologies. Enzymes like horseradish peroxidase or alkaline phosphatase can be conjugated to antibodies in order to act as labels in enzyme immunoassays or immunoenzymometric assays which labels are detected with the help of colorimetric, fluorometric or chemiluminometric substrates. Also, fluorescent compounds can be directly conjugated to antibodies and be used in quantitative fluoroimmunoassays or fluoroimmunometric assays where several sophisticated detecting methods have been developed (e.g., delayed fluorescence, fluorescence polarization). Together with the fluorescence methods, methods using luminescence producing labels (luminescence immunoassays or immunoluminometric assays) are the most sensitive immunochemical technologies available today.

Site-specific and screening tests for determining periodontal disease activity

All the test methods described above can in principle be used in both site-specific and screening tests. However, visual agglutination, flow-through and immunochromatographic methods are best suited to a rapid chair-side test. These techniques are optional for both site-specific and screening tests.

In a screening test the aim is to find out if increased total MMP-8 is present in the patient's gingival crevicular fluid, saliva or mouthrinse samples. If total and active MMP-8 are measured at the same time, an estimate can be made of the stage of progression of the possible periodontal disease.

Saliva is easily collected after letting the patient first rinse his mouth thoroughly and then chewing paraffin. Other stimulants of saliva excretion can also be used. If it is necessary to store the specimen before analysis, a specific saliva collection device like Omni-SAL® (Saliva Diagnostic Systems, Wash.) can be used. Alternatively, the test can be performed in a mouthrinse specimen which is collected by allowing patients to chew paraffin for 30 sec–1 min and subsequently spit the oral fluid contents; thereafter, the patients rinse their empty mouths with 3 ml of tap water which is then collected for testing.

For a site-specific dipstick test, the dentist can collect a sample gingival crevicular fluid by placing a filter paper strip at the periodontal pocket orifice. The strip is allowed to absorb liquid, for a standardized time. Then, the strip is transferred to a test tube with an adequate buffer solution where sample proteins are extracted. In case an immunochromatographic dipstick format is used, the dipstick is directly dipped into the tube for the test. Besides the filter strips other absorbing materials like porous plastics or ceramics as well as organic or inorganic silica compounds are also applicable, e.g. attached to a holder for convinient transfer. Liquid can be collected in a capillary tube of glass or plastic. Finally, a dipstick-type device can be so designed that it includes an absorbing end that is placed in the periodontal pocket and the sample is absorbed directly into test device.

A site-specific dipstick test for ruling out the possibility of periodontal disease in the individual site or directing the clinician to further studies can be quantified. The threshold value (cut-off concentration) for the test is chosen so as to give optimal sensitivity and specificity. In the case a periodontal disease activity test, total MMP-8 concentrations above about 100 ng/ml can be interpreted as positive in site specific samples. The corresponding values in salivary/mouthrinse samples are much more variable. Thus, in saliva/mouthrinse, values of above 100–200 ng/ml of total MMP-8 may suggest an increased risk of progressing periodontitis. A concentration of active MMP-8 above 100 ng/ml in a salivary sample indicates active disease in some sites which should then be individually tested. However, the difference between the values of active MMP-8 from healthy controls and peridontitis patient site-specific is much more distinct. Values of about 1000 ng/ml in a site specific gingival crevicular fluid is a clear indication of progressing periodontitis. In a dipstick test both total and specific tests can be connected in one stick by applying two antibody lines with antibodies having different specificities. This test (from gingival crevicular fluid, saliva, mouthrinse samples) is a new approach and will be used for detecting periodontal sites exhibiting risk for development of both periodontal attachment loss and alveolar bone loss, thus the possible periodontal disease activity in different periodontitis and peri-implantitis patient groups.

We claim:

1. A test kit for diagnosing periodontal disease, peri-implantitis or HIV(+)-infection/AIDS-disease related periodontal diseases comprising at least one detectable label and at least one monoclonal antibody of which at least one specifically recognizes a tissue destructive active form of mammalian matrix metalloproteinase-8 (MMP-8) in gingival crevicular fluid, saliva or mouthrinse samples, said at least one monoclonal antibody being directed against a part of said MMP-8 which is exposed during activation of said MMP-8 from the proenzyme form, and wherein an increased level of MMP-8 indicates periodontal disease.

2. The test kit of claim 1, wherein at lease one of the monoclonal antibodies recognising MMP-8 is a monoclonal antibody obtainable by a method comprising the steps of:
    (a) activating mammalian matrix metalloproteinase-8 proenzyme;
    (b) immunizing mice with a mixture of different isoforms of active matrix metalloproteinase-8 obtainable in step (a);
    (c) producing hybridoma cell lines from mice immunized in step (b); and
    (d) screening for hybridoma cell lines produced in step (c) for monoclonal antibodies that specifically recognize a tissue destructive active form of mammalian matrix metalloproteinase-8 in gingival crevicular fluid, saliva or mouthrinse samples, said monoclonal antibodies being directed against a part of said MMP-8 which is exposed during activation of said MMP-8 from the proenzyme form.

3. The test kit of claim 1, which additionally comprises a second antibody which reacts with a mammalian matrix metalloproteinase-8 proenzyme.

4. The test kit of claim 3, wherein the second antibody is a monoclonal antibody.

5. The test kit of claim 3, wherein the second antibody is a polyclonal antibody.

6. The test kit of claim 1, wherein said mammalian matrix metalloproteinase-8 is human matrix metalloproteinase-8.

7. The test kit of claim 1, wherein the kit is constructed for an immunological method selected from a group consisting of immunochromatographic methods, immunometric methods, radioimmunoassays, radioimmunometric assays, enzyme immunoassays, fluoroimmunoassays, luminescence immunoassays, immunoagglutination, hemagglutination, inhibition of agglutination, turbidimetric immunoassays and nephelometric immunoassays and detectable labels and optional carriers are selected according to the method used.

8. The test kit of claim 7, wherein the kit is constructed for an immunochromatographic method based on a lateral flow principle.

9. The test kit of claim 7, wherein the kit is constructed for an immunological method based on a flow-through principle.

10. The test kit of claim 3, wherein the second antibody is selected from a group, consisting of a polyclonal antibody and a monoclonal antibody, which polyclonal and monoclonal antibody recognizes both active mammalian matrix metalloproteinase-8 and inactive mammalian matrix metalloproteinase-8 proenzyme.

11. The test kit of claim 10, wherein the second does not differentiate between active matrix metalloproteinase-8 and inactive matrix metalloproteinase-8 proenzyme.

12. The test kit of claim 1 which additionally comprises means for site-specific detection by collecting the sample with a solid absorbent sampling device.

13. The test kit of claim 12, wherein the test for diagnosing is performed on the sampling device.

14. The test kit of claim 1, in which said detectable label is selected from the group consisting of a direct and an indirect label.

15. The test kit of claim 1 comprising optional solid or liquid carriers.

16. A method for diagnosing periodontal disease, peri-implantitis or HIV(+)-infection/AIDS-disease related periodontal diseases, wherein the detection is performed as an immunological assay comprising the steps of:

(a) collecting a gingival crevicular fluid sample with a sampling device;

(b) contacting said sample with at least one monoclonal antibody, which recognizes a tissue destructive active form of mammalian matrix metalloproteinase-8 in gingival crevicular fluid, saliva or mouthrinse samples, said monoclonal antibodies being directed against a part of said MMP-8 which is exposed during activation of said MMP-8 from the proenzyme form; and (c) detecting the presence of said active mammalian matrix metalloproteinase-8, wherein an increased level of MMP-8 indicates periodontal disease.

17. The method of claim 16, which additionally comprises a second antibody, which recognises mammalian matrix metalloproteinase-8 proenzyme.

18. The method of claim 17, wherein the second antibody is a monoclonal antibody.

19. The method of claim 17, wherein the second antibody is a polyclonal antibody.

20. The method of claim 17, wherein the second antibody is labeled with a label selected from the group consisting of direct and indirect labels.

21. The method of claim 16, wherein said mammalian matrix metalloproteinase-8 is a human matrix metalloproteinase-8.

22. The method of claim 16, in which the sample is selected from the group consisting of site-specific gingival crevicular fluid, salivary and mouthrinse samples.

23. The method of claim 16, wherein said immunological assay is used for assessing the progress of periodontal disease activity.

24. A method for prescreening for the risk of periodontal disease, peri-implantitis or HIV(+)-infection/AIDS-disease related periodontal diseases, wherein the detection is performed as an immunological assay comprising the steps of:

(a) collecting a sample containing gingival crevicular fluid;

(b) contacting said sample with at least one monoclonal antibody, which recognises a tissue destructive form of mammalian matrix metalloproteinase-8 in gingival crevicular fluid, saliva or mouthrinse sample, said monoclonal antibody being directed against a part of said MMP-8 which is exposed during activation of said MMP-8 from the proenzyme form; and (c) detecting the presence of said mammalian matrix metalloproteinase-8 by the aid of an immunological method capable of recognizing an increased level of matrix metalloproteinase-8 wherein an increased level of MMP-8 indicates a risk for said diseases.

* * * * *